United States Patent [19]

Saito et al.

[11] Patent Number: 5,325,416
[45] Date of Patent: Jun. 28, 1994

[54] METHOD FOR MEASURING FE COATING WEIGHT OF FE-COATED STAINLESS STEEL SHEET

[75] Inventors: Minoru Saito, Izumiotsu; Kazuaki Hosomi, Amagasaki; Toshiharu Kitsutaka, Kishiwada, all of Japan

[73] Assignee: Nisshin Steel Co., Ltd., Tokyo, Japan

[21] Appl. No.: 140,551

[22] Filed: Oct. 25, 1993

[51] Int. Cl.$^5$ .......................................... G01N 23/223
[52] U.S. Cl. ................................. 378/50; 378/44
[58] Field of Search ................ 378/44, 50, 54, 59, 378/89

[56] References Cited

U.S. PATENT DOCUMENTS 5,081,658 1/1992 Imai et al. .......................... 378/44

OTHER PUBLICATIONS

H. F. Beeghly, "An X-Ray Method for Determining Tin Coating Thickness", Apr. 1950, vol. 97, No. 4, 152-157.

Primary Examiner—David P. Porta
Assistant Examiner—Don Wong
Attorney, Agent, or Firm—Foley & Lardner

[57] ABSTRACT

The surface of a stainless steel sheet before Fe-coating and the surface of the same stainless steel sheet after Fe-coating are analyzed by X-ray fluorescent analysis to determine the ratio of a fluorescent X-ray intensity $I_{Cr}b$ ascribable to CF to a fluorescent X-ray intensity $I_{Fe}b$ ascribable to Fe before Fe-coating, $I_{Cr}b/I_{Fe}b$, and the ratio of a fluorescent X-ray intensity $I_{Cr}a$ ascribable to Cr to a fluorescent X-ray intensity $I_{Fe}a$ ascribable to Fe after Fe-coating, $I_{Cr}a/I_{Fe}a$, and the resulting values are substituted in the following equation to calculate an Fe coating weight W (g/m$^2$).

$$W=(I_{Cr}b/I_{Fe}b - I_{Cr}a/I_{Fe}a)/C$$

wherein C represents a proportional constant determined by the type of steel of a stainless steel sheet.

2 Claims, 5 Drawing Sheets

METHOD FOR MEASURING FE COATING WEIGHT OF FE-COATED STAINLESS STEEL SHEET

BACKGROUND OF THE INVENTION

This invention relates to a method that can measure Fe coating weight of an Fe-coated stainless steel sheet at the same time when Fe-coating is carried out.

Stainless steel sheets have superior corrosion resistance and heat resistance. Application of hot dip coating of Al or the like to stainless steel sheets can bring about a more improvement in corrosion resistance and heat resistance. This hot dip coating is carried out by the same coating method as in the hot dip coating on low-carbon steel sheets. This method commonly includes a method in which oily deposits such as rolling mill lubricants and rust preventives having adhered to the surface of a base steel sheet are first removed in a non-oxidizing furnace or degreasing device of a continuous hot dip coating line and then the Fe oxide on the surface is reduced in a high-temperature $H_2$—$N_2$ atmospheric gas, followed by hot dip coating of Al or the like. When, however, the hot dip coating is applied to stainless steel sheets by this method, Cr contained in stainless steel sheets may thermally diffuse at the time of the reduction to concentrate toward the surface, so that it preferentially undergoes oxidation to cause damage of wettability to molten metals, resulting in occurrence of surface defects such as non-coating.

Accordingly, when hot dip coating is applied to stainless steel sheets, Fe is previously coated in a continuous electroplating line in a coating weight of 0.05 to 5 $g/m^2$ to make their surfaces have the same properties as those of low-carbon steel sheets, followed by hot dip coating in a continuous hot dip coating line. This Fe pre-coating is applied to improve the wettability of stainless steel sheets to molten metals. Hence, in order to produce hot dip coated stainless steel sheets at a low cost, it is preferable to make the Fe coating weight smallest so long as no surface defects may occur.

For measuring this Fe coating weight, no method for accurately measuring it at the same time when Fe-coating is carried out in a continuous electroplating line has been hitherto available. Accordingly, the Fe coating weight has been measured by a gravimetric analysis in which a sample is taken and its Fe coating layer is dissolved with an aqueous nitric acid solution so that the coating weight is calculated from a difference in weight before and after the dissolution.

In this gravimetric analysis, however, the sampling has been limited to tops and ends of Fe coated stainless steel sheet coils and no coating weight can be ascertained on the lengthwise extent of Fe coated stainless steel sheet coils. Hence, it has been common to apply Fe-coating in a little larger coating weight to prevent shortage of coating weight. This has brought about the problem that Fe-coating results in a high cost. There has been another problem that, because of a long time taken after the sampling until measurements come out, no immediate adjustment can be made even if the coating weight has been found excessive or insufficient. There has been still another problem that this gravimetric analysis can not be used when a continuous electroplating line is set on the inlet side of a continuous hot dip coating line so that Fe pre-coating and hot dip coating can be simultaneously carried out in order to improve productivity, because samples can not be taken for only Fe pre-coating.

As measurement of coating weight not relying on the gravimetric analysis, X-ray fluorescent analysis is known in the art. This is a method in which the fluorescent X-ray intensity ascribable to an element constituting a base stainless steel sheet or the fluorescent X-ray intensity ascribable to an element mainly constituting a coating layer is measured and the measurements are substituted in a fluorescent X-ray intensity equation to calculate the coating weight. Hence, this requires no sampling, and may be considered feasible for continuous measurement of the coating weight.

This method, however, is not feasible for measurement of coating weight since, when both a base stainless steel sheet and a coating layer contain Fe as in the case of Fe-coated stainless steel sheets, the fluorescent X-ray intensities ascribable to Fe contained in the both can not be separated. Thus, this method can only be applied to instances in which metals different from the components of base sheets are coated.

SUMMARY OF THE INVENTION

A first object of the present invention is to provide a method for measuring Fe coating weight even on an Fe-coated stainless steel sheet both the base stainless steel sheet and the coating layer of which contain Fe.

A second object of the present invention is to provide a method that can continuously measure Fe coating weight at the same time with Fe-coating when the Fe-coating is continuously carried out.

The present invention is characterized by analyzing the surface of a stainless steel sheet by X-ray fluorescent analysis before Fe-coating and the surface of the same stainless steel sheet after Fe-coating to determine the ratio of a fluorescent X-ray intensity $I_{Cr}b$ ascribable to Cr to a fluorescent X-ray intensity $I_{Fe}b$ ascribable to Fe before Fe-coating, $I_{Cr}b/I_{Fe}b$, and the ratio of a fluorescent X-ray intensity $I_{Cr}a$ ascribable to Cr to a fluorescent X-ray intensity $I_{Fe}a$ ascribable to Fe after Fe-coating, $I_{Cr}a/I_{Fe}a$, and substituting the resulting values in the following equation to calculate an Fe coating weight W ($g/m^2$).

$$W = (I_{Cr}b/I_{Fe}b - I_{Cr}a/I_{Fe}a)/C$$

wherein C represents a proportional constant determined by the type of steel of a stainless steel sheet.

DESCRIPTION OF THE PREFERRED EMBODIMENTS

The present inventors examined fluorescent X-ray intensities ascribable to Fe and Cr of Fe-coated stainless steel sheets to find a way enabling application of X-ray fluorescent analysis that has been difficult to apply in the measurement of Fe coating weight of Fe-coated stainless steel sheets. As a result, they have discovered that with an increase in Fe coating weight the fluorescent X-ray intensity ascribable to Fe monotonously increases and inversely the fluorescent X-ray intensity ascribable to Cr monotonously decreases. Then, they studied the ratio of fluorescent X-ray intensity ascribable to Cr to that ascribable to Fe (hereinafter often "Cr/Fe fluorescent X-ray intensity ratio"). As a result, they have discovered that the ratio linearly decreases with an increase in Fe coating weight in accordance with the types of steel of stainless steel sheets and its relationship can be approximated by a simple equation, and that the utilization of this relationship enables application of X-ray fluorescent analysis in the measurement of Fe coating weight of Fe-coated stainless steel sheets. The present invention will be described below in detail.

Figure 1:
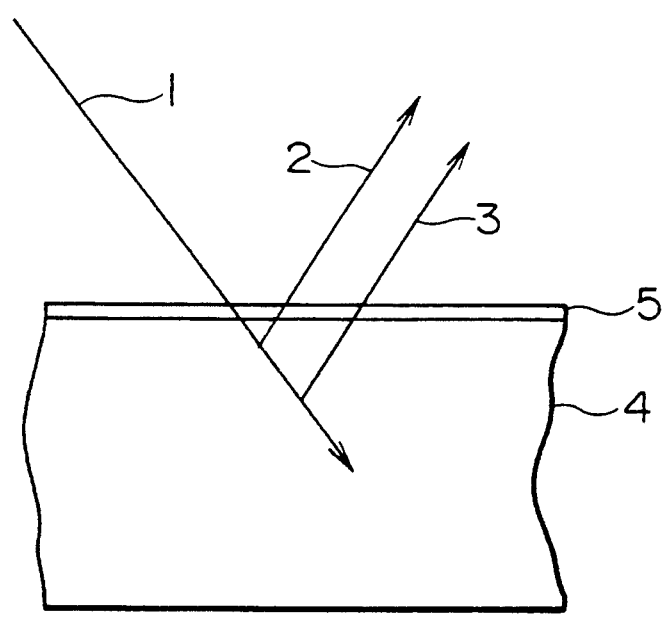
FIG. 1 shows fluorescent X-rays pertaining to Fe and Cr, produced when an Fe-coated stainless steel sheet is irradiated with X-rays.

As shown in FIG. 1, upon irradiation of the surface of an Fe-coated stainless steel sheet with primary X-rays 1, fluorescent X-rays 2 pertaining to Fe and fluorescent X-rays 3 pertaining to Cr are secondarily produced. The fluorescent X-rays 2 pertaining to Fe to be detected correspond to the total of X-rays coming from a stainless steel sheet 4 and an Fe coating layer 5 as previously stated. On the other hand, the fluorescent X-rays 3 pertaining to Cr to be detected are X-rays coming from only the stainless steel sheet 4.

Figure 2:
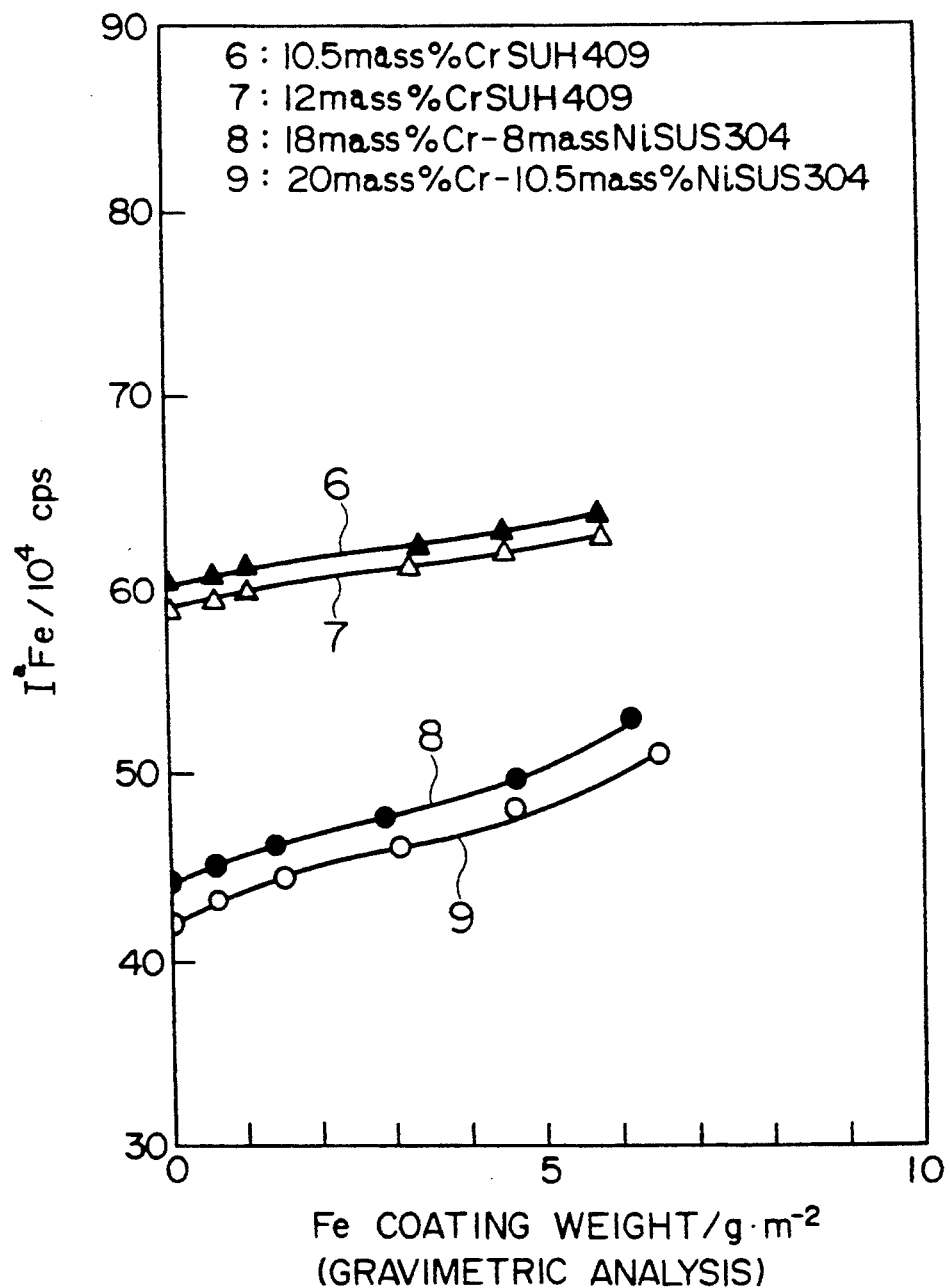
FIG. 2 is a graph to show the relationship between Fe coating weight of an Fe-coated stainless steel sheet and fluorescent X-ray intensity ascribable to Fe, for each type of stainless steel and production lot.
Figure 3:
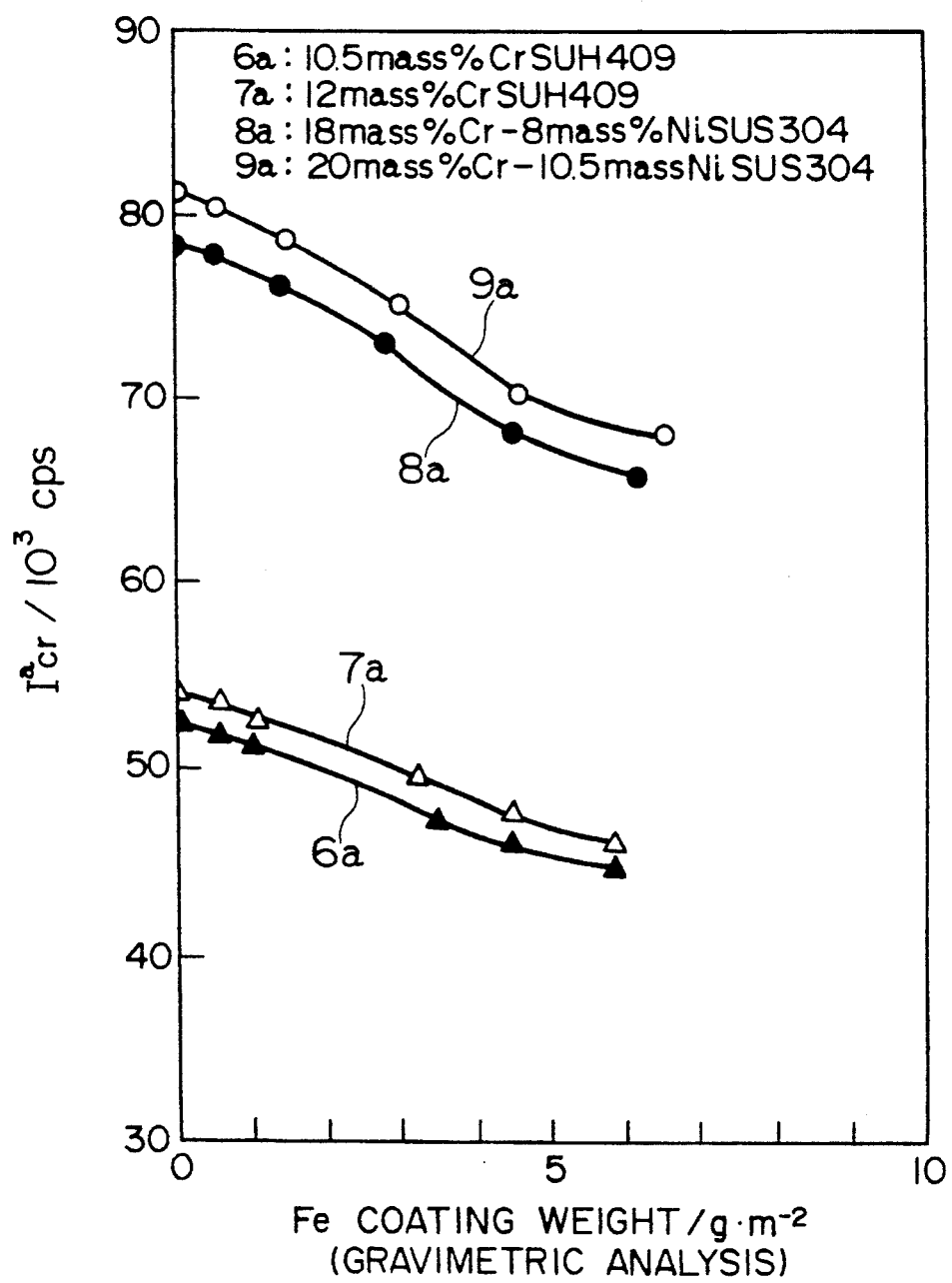
FIG. 3 is a graph to show the relationship between Fe coating weight of an Fe-coated stainless steel sheet and fluorescent X-ray intensity ascribable to Cr, for each type of stainless steel and production lot.

Examination of the relationship between fluorescent X-ray intensity $I_{Fe}a$ ascribable to Fe, corresponding to that total, and Fe coating weight and the relationship between fluorescent X-ray intensity $I_{Cr}a$ ascribable to Cr and Fe coating weight has been made for each type of stainless steel and production lot (Cr concentration) to reveal that, as shown in FIG. 2, the former fluorescent X-ray intensity monotonously increases with an increase in Fe coating weight and on the other hand, as shown in FIG. 3, the latter fluorescent X-ray intensity monotonously decreases with an increase in Fe coating weight, in each type of stainless steel and production lot. In FIGS. 2 and 3, graphs 6 and 6a pertain to an Fe-coated 10.5 mass % Cr stainless steel sheet of Japan Industrial Standard SUH409 (corresponding to Type 409 of AISI); graphs 7 and 7a, an Fe-coated 12 mass % Cr stainless steel sheet of SUH409; graphs 8 and 8a, an Fe-coated 10.5 mass % Cr/8. mass % Ni stainless steel sheet of Japan Industrial Standard SUS304 (corresponding to Type 304 of AISI); and graphs 9 and 9a, an Fe-coated 20 mass % Cr/8 mass % Ni stainless steel sheet of SUS304. The fluorescent X-ray intensities $I_{Fe}a$ and $I_{Cr}a$ ascribable to Fe and Cr, respectively, are both intensities of Kα-rays.

Hence, the Fe coating weight can be measured if the relationship as shown in FIG. 2 or 3 is set up for each Fe concentration or Cr concentration of each type of stainless steel and the resulting data are represented by a calibration curve equation. However, in order to make up a calibration curve equation for every Fe concentration or Cr concentration of every type of stainless steel, the Fe concentrations and Cr concentrations of stainless steel sheets must be individually measured by chemical analysis. This requires an enormous amount of work.

Figure 4:
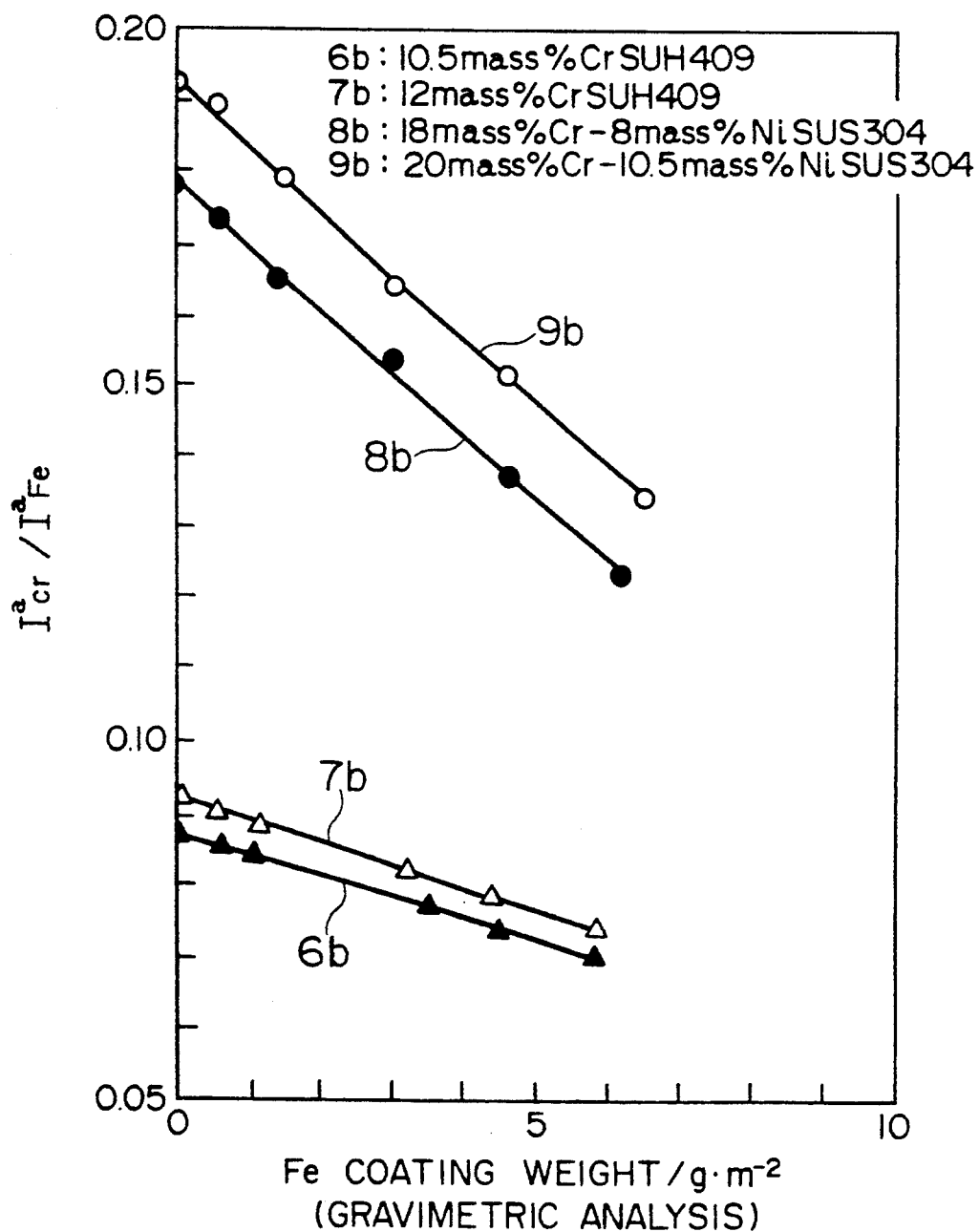
FIG. 4 is a graph to show Fe coating weight of an Fe-coated stainless steel sheet and the relationship between fluorescent X-ray intensity ascribable to Fe and that to Cr, for each type of stainless steel and production lot.

Now, the present inventors newly took note of the ratio of a fluorescent X-ray intensity $I_{Cr}a$ ascribable to Cr to a fluorescent X-ray intensity $I_{Fe}a$ ascribable to Fe, $I_{Cr}a/I_{Fe}a$, and adjusted the data shown in FIGS. 2 and 3 to have discovered that as shown in FIG. 4 the intensity ratio $I_{Cr}a/I_{Fe}a$ linearly decreases with an increase in Fe coating weight and its gradient becomes constant in accordance with the type of stainless steel without regard to the production lot, in other words, the gradient becomes constant without regard to the Fe concentration or Cr concentration of stainless steel sheets so long as the type of stainless steel is the same. In FIG. 4, graphs 6b, 7b, 8b and 9b pertain to a 10.5 mass % Cr SUH409 stainless steel sheet, a 12 mass % Cr SUH409 stainless steel sheet, a 20 mass % Cr/8 mass % Ni SUS304 stainless steel sheet and a 18 mass % Cr/10.5 mass % Ni SUS304 stainless steel sheet, respectively, used as base stainless steel sheets.

The reason why the gradient of the intensity ratio $I_{Cr}a/I_{Fe}a$ differs in accordance with the type of stainless steel is as follows: Since the fluorescent X-ray intensity $I_{Fe}a$ ascribable to Fe to be detected is a total intensity of the X-rays coming from both a base stainless steel sheet and a coating layer, the intensity of X-rays coming from the base stainless steel sheet is held in a smaller proportion in the fluorescent X-ray intensity $I_{Fe}a$ ascribable to Fe and the intensity of X-rays coming from the Fe coating layer is held in a larger proportion, when the base stainless steel sheet has a low Fe concentration as the SUS304 stainless steel sheet does. Hence, the fluorescent X-ray intensity $I_{Fe}a$ ascribable to Fe greatly changes with a change in Fe coating weight. For this reason, in the case of the SUS304 stainless steel sheet, the gradient of the intensity ratio $I_{Cr}a/I_{Fe}a$ becomes larger as shown by graph 8b and graph 9b. On the other hand, when the base stainless steel sheet has a high Fe concentration, the intensity of X-rays coming from the base stainless steel sheet is held in a larger proportion, and hence the change in the fluorescent X-ray intensity $I_{Fe}a$ ascribable to Fe is small even if the Fe coating weight changes, resulting in a smaller gradient as shown by graph 6b and graph 7b.

Incidentally, since the gradients are equal to each other when the type of stainless steel is the same, the graphs in FIG. 4 can be expressed by the following regression line equation.

$$I_{Cr}a/I_{Fe}a = I_{Cr-0}/I_{Fe-0} - C \cdot W \tag{1}$$

wherein;

$I_{Cr}a/I_{Fe}a$ represents a Cr/Fe fluorescent X-ray intensity ratio after Fe-coating;

$I_{Cr-0}/I_{Fe-0}$ represents a Cr/Fe fluorescent X-ray intensity ratio when Fe coating weight is 0 g/m²;

W represents a Fe coating weight (g/m²) measured by the gravimetric analysis; and C represents a proportional constant in accordance with the type of steel of a stainless steel sheet.

Since, however, according to this regression line equation the gradient may differ depending on the Fe concentration or Cr concentration in the base stainless steel sheet, the Cr/Fe fluorescent X-ray intensity ratio $I_{Cr}a/I_{Fe}a$ differs depending on the production lot even when base stainless steel sheets are of the same type and have the same Fe coating weight. Hence, an error may occur depending on the Fe concentration or Cr concentration in the base stainless steel sheet if the Fe coating weight is measured by a calibration curve equation according to one regression line equation for each type of stainless steel.

This error can be prevented by measuring the Cr/Fe fluorescent X-ray intensity ratio of a stainless steel sheet before Fe-coating, to determine the Cr/Fe fluorescent X-ray intensity ration $I_{Cr}a/I_{Fe}a$ in the above equation (1) when Fe coating weight is 0 g/m$^2$, and setting up a regression line equation corresponding to the Fe concentration or Cr concentration for each type of stainless steel. For example, in Fe-coating carried out using a 10.5 mass % Cr SUH409 stainless steel sheet as the base stainless steel sheet, the Cr/Fe fluorescent X-ray intensity ratio as measured on the base stainless steel sheet before Fe-coating comes to be about 0.088, and hence the regression line equation gives the graph 6b shown in FIG. 4.

Therefore, when the Cr/Fe fluorescent X-ray intensity ratio of the base stainless steel sheet before Fe-coating is represented by $I_{Cr}b/I_{Fe}b$ and the resulting value is substituted for $I_{Cr-0}/I_{Fe-0}$ in the formula (1) to make an adjustment on W, the Fe coating weight W can be measured by making a calculation according to the following equation.

$$W = (I_{Cr}b/I_{Fe}b - I_{Cr}a/I_{Fe}a)/C \quad (2)$$

An example of the measurement made at the same time with Fe-coating in a continuous Fe-electroplating line will be described below. Referring first to fluorescent X-rays for detecting Fe and Cr, there are no particular limitations thereon. They may preferably be K$\alpha$-rays, having a large intensity and not liable to be absorbed in substances. Fluorescent X-ray spectrometry can be grouped into an energy dispersion system and a wavelength dispersion system. The latter is preferred, having a superiority in resolving power. There are no particular limitations also on excitation sources. Preferred are X-rays, which can be handled with ease.

Figure 5:
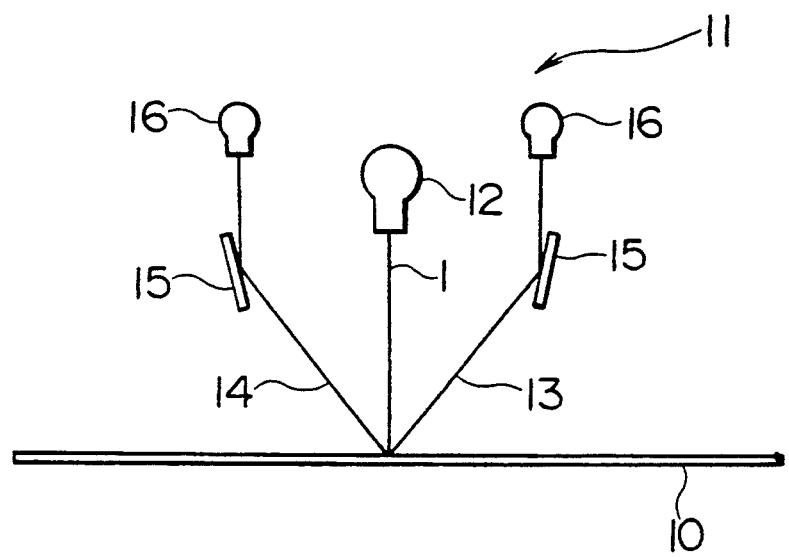
FIG. 5 illustrates a method for measuring fluorescent X-ray intensities on a base stainless steel sheet and an Fe-coated stainless steel sheet.

The Cr/Fe fluorescent X-ray intensity ratio $I_{Cr}b/I_{Fe}b$ the base stainless steel sheet or the Cr/Fe of fluorescent X-ray intensity ratio $I_{Cr}a/I_{Fe}a$ after Fe-coating can be measured in the following way: As shown in FIG. 5, a measuring head 11 is provided at the upper part of a stainless steel sheet 10 to be measured, and primary X-rays 1 as an excitation source are generated from an X-ray tube 12 to the surface of the stainless steel sheet 10. The resulting fluorescent X-rays (K$\alpha$-rays) 13 pertaining to Cr and fluorescent X-rays (K$\alpha$-rays) 14 pertaining to Fe are spectrally analyzed through an analyzing crystal 15, and thereafter fluorescent X-ray intensities ascribable to Cr and Fe are measured by means of a detector 16.

Figure 6:
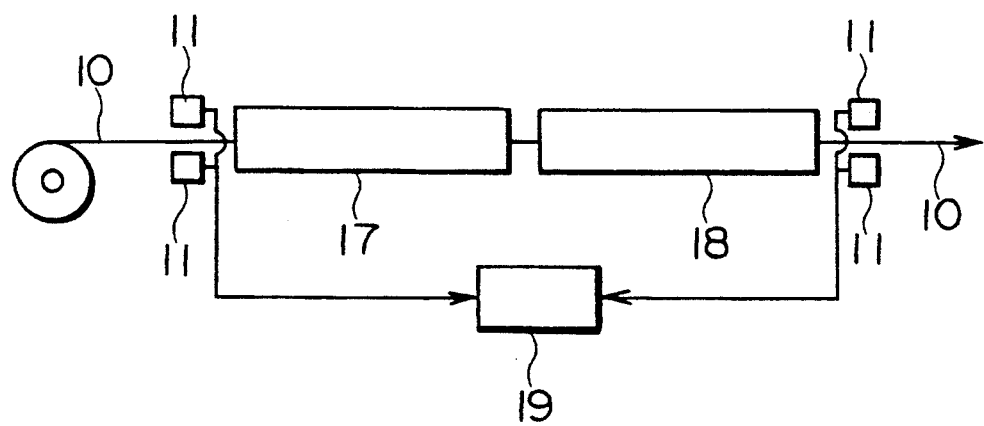
FIG. 6 illustrates the method for measuring Fe coating weight according to the present invention, in a continuous Fe-coating line.

The measuring head 11 is, as shown in FIG. 6, provided at each position of the inside and outside of both the inlet side and the outlet side of the continuous Fe-electroplating line so that the fluorescent X-ray intensities ascribable to Cr and Fe can be measured before and after the Fe-coating on the same base stainless steel sheet. The measuring heads 11 are so provided that the inside and outside measurement positions are at the same spot before or after the Fe-coating, and the measurement is carried out while they are made to traverse in the direction of sheet width. Reference numeral 17 denotes an electrolytic degreasing bath, and 18, an Fe electroplating bath.

The measuring heads 11 are connected to a computer 19 in which the proportional constant C for each type of steel of stainless steel sheets and a computing equation have been imputted, where the Fe coating weight is calculated and the calculations are fed back to control coating conditions. On the outlet side of the continuous Fe-electroplating line, a continuous hot dip coating line may be provided in series.

The base stainless steel sheets contain various additive elements and inevitable impurities in addition to Cr and Fe, depending on the type of stainless steel. These, however, can not be obstacles to the measurement, except for very special occasions. The same also applies to some instances of Fe-coating in which 0.001 to 0.3 mass % of B (boron) is added in order to improve wettability to molten metals when hot dip coating is carried out.

EXAMPLES

The measuring head as shown in FIG. 5 was provided in the manner as shown in FIG. 6. While applying Fe-coating to various types of stainless steel sheets by electroplating under the conditions shown below, the Fe coating weight was measured and the measurements were compared with measurements obtained by the gravimetric analysis. On the samples measured by the gravimetric analysis, sampling was made at the positions random in the line direction of stainless steel sheets at their both sides and middle areas. Fe coating weights measured by the method of the present invention and the gravimetric analysis are shown in Table 1.

(1) Base stainless steel sheets:
)A) Type of stainless steel:
   SUS304 (Type 304 of AISI; Cr: 18 to 20 mass %; Ni: 8 to 10.5 mass %)
   SUS316 (Type 316 of AISI; Cr: 16 to 18 mass %; Ni: 10 to 10.5 mass %)
   SUS409 (Type 409 of AISI; Cr: 10.5 to 12 mass %)
   SUS444 (Type 444 of AISI; Cr: 18 to 20 mass %)
(B) Sheet thickness: 1.0 mm
(C) Sheet width: 1,000 mm
(D) Coil number: 5 coils with different production lots for each stainless steel sheet.
(2) Fe-electroplating conditions:
(A) Plating bath composition:
   300 g/lit. of ferrous sulfate, 70 g/lit. of sodium sulfate, 1 g/lit. of tartaric acid and 5 to 50 g/lit. of boric acid.
(B) pH: 1.5 to 2.0
(C) Bath temperature: 50° C.
(D) Current density: 5,000 A/m$^2$
(E) Fe coating weight: 0.38 to 5.78 g/m$^2$ (Time of electrification was controlled.)
(F) B concentration in Fe coating layer: 0.001 to 0.3 mass % (The amount of boric acid added was controlled.)
(3) Conditions for measurement of Fe coating weight:
(A) X-ray tube: Tungsten
(B) Tube voltage: 50 kV
(C) Tube current: 40 mA
(D) Analyzing crystal: LiF
(E) Detector: Proportional counter
(F) Measurement object: Cr: K$\alpha$-rays, Fe: K$\alpha$-rays
(G) Incident angle of excitation X-rays and measuring angle of fluorescent X-rays: 60°

(H) Measuring time: 1 second (I) Traversing: While reciprocating the measuring heads once a minute in the direction of sheet width, measurement was made at both sides and a middle area of each stainless steel sheet. (The measuring heads were synchronized so that the inside and outside measurement positions are at the same spot before or after the Fe-coating).

TABLE 1

| Type of stainless steel | Top surface Fe-coating Coating weight | | Back surface Fe-coating Coating weight | |
|---|---|---|---|---|
| | X (g/m²) | Y (g/m²) | X (g/m²) | Y (g/m²) |
| SUS304 | 0.54 | 0.49 | 0.68 | 0.74 |
| | 1.09 | 1.10 | 1.22 | 1.12 |
| | 2.22 | 2.20 | 2.15 | 2.16 |
| | 3.16 | 3.16 | 3.14 | 8.24 |
| | 5.18 | 5.15 | 5.24 | 5.22 |
| SUS316 | 0.44 | 0.47 | 0.38 | 0.46 |
| | 0.99 | 1.00 | 0.96 | 1.05 |
| | 1.97 | 1.89 | 2.00 | 2.10 |
| | 3.01 | 3.08 | 3.10 | 3.05 |
| | 4.86 | 4.99 | 4.76 | 4.77 |
| SUS409 | 0.67 | 0.68 | 0.61 | 0.55 |
| | 1.11 | 1.10 | 1.07 | 1.08 |
| | 1.64 | 1.63 | 1.58 | 1.49 |
| | 3.33 | 3.32 | 3.54 | 3.56 |
| | 5.78 | 5.69 | 5.55 | 5.61 |
| SUS444 | 0.38 | 0.44 | 0.51 | 0.60 |
| | 1.59 | 1.54 | 1.44 | 1.52 |
| | 2.36 | 2.28 | 2.41 | 2.45 |
| | 4.01 | 4.10 | 3.88 | 3.92 |
| | 5.55 | 5.49 | 5.68 | 5.70 |

X: Gravimetric analysis,
Y: Method of the invention

As described above, the present invention makes it possible to measure the Fe coating weight of a stainless steel sheet in its full length at the same time when the Fe-coating is carried out. Hence, the coating weight can be controlled within the intended range in a good precision even when the coating weight is excessive or insufficient. This brings about an improvement in quality of products and a decrease in the cost of Fe-coating. The present method can also be applied also when a continuous electroplating line for Fe-coating and a continuous hot dip coating line are combined to simultaneously carry out Fe-coating and hot dip coating.

What is claimed is:

1. A method fop measuring Fe coating weight of an Fe-coated stainless steel sheet, comprising analyzing the surface of a stainless steel sheet by X-ray fluorescent analysis before Fe-coating and the surface of the same stainless steel sheet after Fe-coating to determine the ratio of a fluorescent X-ray intensity $I_{Cr}b$ ascribable to Cr to a fluorescent X-ray intensity $I_{Fe}b$ ascribable to Fe before Fe-coating, $I_{Cr}b/I_{Fe}b$, and the ratio of a fluorescent X-ray intensity $I_{Cr}a$ ascribable to Cr to a fluorescent X-ray intensity $I_{Fe}a$ ascribable to Fe after Fe-coating, $I_{Cr}a/I_{Fe}a$, and substituting the resulting values in the following equation to calculate an Fe coating weight W (g/m²).

$$W = (I_{Cr}b/I_{Fe}b - I_{Cr}a/I_{Fe}a)/C$$

wherein C represents a proportional constant determined by the type of steel of a stainless steel sheet.

2. A method for measuring Fe coating weight of an Fe-coated stainless steel sheet according to claim 1, wherein the surface of said stainless steel sheet is analyzed by means of a measuring head of an X-ray fluorescent analyzer, provided at the inlet side and outlet side each of a continuous Fe-electroplating line.

* * * * *